Feb. 18, 1964 E. DELP ETAL Plant Pat. 2,365
PEACH TREE
Filed Oct. 10, 1962
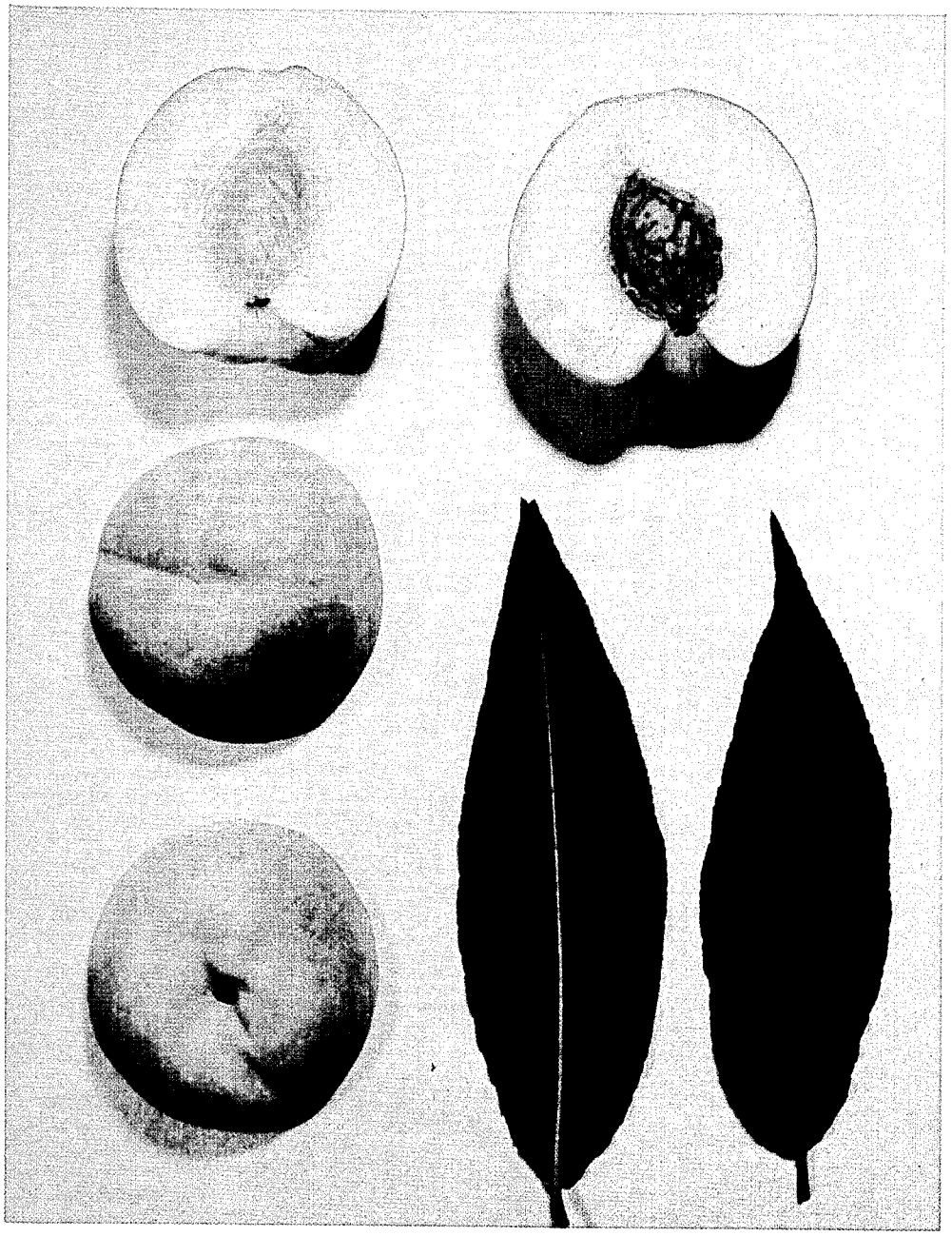
Inventors.
Erwin Delp and
Julia M. Delp
By: Robb & Robb
Attorneys.

United States Patent Office

Plant Pat. 2,365
Patented Feb. 18, 1964

2,365
PEACH TREE

Ervin Delp and Julia M. Delp, both of Rte. 2, Box 120, Wapato, Wash.

Filed Oct. 10, 1962, Ser. No. 229,774
1 Claim. (Cl. Plt.—43)

The present invention relates to a new and distinct variety of peach tree which was discovered by us in our cultivated orchard at Wapato, Washington, as a newly found seedling.

At the time of our initial discovery aforesaid, we were growing various varieties of peach trees in our orchard, including the following: "J. H. Hale"; "Elberta"; "Golden Elberta"; "Slappey"; "Candoka"; "Golden Jubilee" and "Carmen." In the course of our cultivation and care of our orchard, our attention was attracted to a small seedling which we discovered growing under one of the trees of the "J. H. Hale" variety, and which was bearing ripe fruit while the fruit of the "J. H. Hale" tree was still green. The color of the fruit of the new seedling was a beautiful deep red and a more golden color than that of any peaches we had ever previously seen. On sampling the fruit of the new seedling, we found that the flavor was delicious, and that the texture of the flesh was firmer than that of "Elberta" varieties, but not as fibrous as "J. H. Hale" fruit.

After our initial discovery and preliminary observations, we transplanted the new seedling to a more appropriate and accessible location, and continued to observe the same and more extensively test the fruit, which tests included canning and freezing. As the result, we were so impressed with the excellent quality, early maturity and durability of the new variety that we budded sufficient additional trees in order to make further observations and tests on a more extensive basis.

Continued observations of the original seedling, as well as the asexually reproduced trees, convinced us that our newly found seedling was a new and distinct variety, presumably originating from open-pollination of the "J. H. Hale" variety or one of the other varieties then being grown by us in our orchard at Wapato, Washington, but from which the new variety is clearly differentiated, as well as from all other varieties of which we are aware, as evidenced by the following unique combination of characteristics which are outstanding in the new variety:

(1) Large leaves;

(2) A habit of blooming at the same time as "J. H. Hale," and the ability to pollinate the "J. H. Hale" variety, as well as being self-pollinating;

(3) A relatively even spacing of the buds;

(4) Early maturity of the fruit, ranging from about 10 days to two weeks earlier than "J. H. Hale," which is an important advantage commercially due to the preference of growers in more recent years for varieties which bear early maturing fruit;

(5) Very fine textured and firm fruit of good flavor and good shipping and canning qualities, with the fruit having the color of "Golden Elberta" (unpatented) when canned and does not lose any of its color or flavor, yet has the good shipping qualities of "J. H. Hale";

(6) The ability of the fruit to hang on the tree until very ripe without dropping; and (7) A distinctive, attractive and high fruit color which is deep red on one side and golden yellow on the other side.

Asexual reproduction of our new variety by budding, as performed by us at Wapato, Washington, shows that the foregoing characteristics and distinctions come true to form and are established and transmitted through succeeding propagations.

The accompanying drawing shows typical specimens of the foliage and fruit of our new variety as depicted in color as nearly true as it is reasonably possible to make the same in a color illustration of this character, said fruit being shown in elevation and also in cross-section, with one half-section exposing the cavity and the other half-section exposing the stone seated in the cavity, and the foilage specimens depicting both the upper and under surfaces of typical leaves.

The following is a detailed description of the new variety, with color terminology in accordance with the Munsell Color Chart, published by Munsell Color Company, Inc., of Baltimore, Maryland, except where general color terms of ordinary dictionary significance are obvious:

Locality where grown and observed: Wapato, Washington.

Dates of first and last pickings: August 6 and August 15, respectively.

Tree: Large; vigorous; open; spreading; round-topped; hardy; very productive; regular bearer.

*Trunk.*—Stocky; medium smoothness.

*Branches.*—Stocky; smooth. Color—brown. Lenticels—medium thickness; medium smoothness.

*Leaves.*—Large; lanceolate; acutely pointed; thick; smooth. Length—about 6 inches. Width—from about 1½ inches to 2 inches. Color: upper surface—Moderate Olive Green, Plate 5GY 4/3; under surface—Moderate Yellow Green, Plate 5GY 5/6. Margin—glandular; finely serrate. Petiole—medium length; thick. Glands—average 3 in number; alternate; small; reniform; appressed; smooth.

Flower:

*Dates of first and full bloom.*—April 5 and April 12, respectively.

*Size.*—Medium.

*Color.*—Pale pink.

Fruit:

*Maturity when described.*—Eating-ripe. Date—August 15. *Size.*—Uniform; medium-large. Axial diameter—about 2¾ inches. Transverse diameter in suture plane—about 2¾ inches. Diameter at right angles to suture plane—about 2¾ inches.

*Form.*—Uniform; symmetrical; globose; spherical; compressed laterally toward suture; sides equal.

*Suture.*—Shallow and indistinct, but deep near pistil, and has slightly marked depression beyond pistil point.

*Ventral surface.*—Slightly lipped toward base; lips equal.

*Cavity.*—Abrupt; suture shows on one side. Depth—about ½ inch. Breadth—about ½ inch.

*Base.*—Rounded.

*Apex.*—Rounded; pistil point apical.

*Stem.*—Stout; glabrous; strong adherence to stone. Length—about ¼ inch.

*Skin.*—Medium thickness; tough; neither astringent nor bitter; medium-tenacious to flesh; no tendency to crack. Color—blush of Strong Red, Plate 5R 4/12, with under color of Dark Orange Yellow, Plate 10YR 6/8. Down—short; slightly pubescent; does not roll up when rubbed.

*Flesh.*—Color—Dark Orange Yellow, Plate 10YR 6/8, with slight red color next to stone.

*Amygdalin.*—Scant.

*Juice.*—Abundant; rich.

*Texture.*—Firm; melting.

*Fibres.*—Few; fine; tender.

*Ripens.*—Fairly even.
*Flavor.*—Moderately strong; slightly acid.
*Aroma.*—Distinct.
*Eating quality.*—Good.

Stone: Free; does not tend to split like many other varieties, as compared with various varieties grown by us in our orchard under the same condition at Wapato, Washington, all of which had extensive split pits, with consequent heavy down-grading of commercial fruit.

*Size.*—Medium. Length—about 1½ inches. Thickness—about ¾ inch.
*Fibres.*—Short; retains short fibre-like threads along ridges.
*Form.*—Ovoid; full.
*Base.*—Straight; narrow; oblong.
*Apex.*—Acuminate.
*Sides.*—Equal.
*Surface.*—Regularly furrowed and pitted throughout.
*Ridges.*—Rounded toward base.
*Pits.*—Circular.
*Ventral edge.*—Medium thin; with wing throughout.
*Dorsal edge.*—Narrow, shallow grooved throughout; ridges continuous.

Insect and disease resistance: Good resistance to common insects and diseases to which peach varieties are normally subject in the area of Wapato, Washington, as determined by comparison with other varieties grown under the same cultural conditions at Wapato, Washington.

Use: Local and distant fresh fruit markets; canning; freezing; other processing.
Keeping Quality: Good.
Shipping Quality: Good.

We claim:

A new and distinct variety of peach tree of the yellow-fleshed freestone fruit-bearing class, substantially as herein shown and described, characterized particularly as to novelty by the unique combination of large leaves, a habit of blooming at the same time as the variety "J. H. Hale" (unpatented) and the ability to pollinate the "J. H. Hale" variety, as well as being self-pollinating, a relatively even spacing of the buds, early maturity of the fruit ranging from about ten days to two weeks earlier than "J. H. Hale," very fine textured and firm fruit of good flavor and good keeping, shipping, canning and freezing qualities, the ability of the fruit to hang on the tree until very ripe without dropping, and a distinctive, attractive and high fruit color corresponding to deep red on one side and golden on the other side.

No references cited.